United States Patent [19]

Belanger

[11] Patent Number: 4,727,562
[45] Date of Patent: Feb. 23, 1988

[54] MEASUREMENT OF SCATTER IN X-RAY IMAGING

[75] Inventor: Barry F. Belanger, Milwaukee, Wis.

[73] Assignee: General Electric Company, Milwaukee, Wis.

[21] Appl. No.: 776,394

[22] Filed: Sep. 16, 1985

[51] Int. Cl.$^4$ .................................... G01N 23/02
[52] U.S. Cl. ............................ 378/99; 378/7; 378/145; 378/147
[58] Field of Search ............... 378/7, 99, 145, 147, 378/86, 87

[56] References Cited

U.S. PATENT DOCUMENTS 4,087,837 5/1978 Geluk ...................... 378/99
4,549,307 10/1985 Macouski .................. 378/99

Primary Examiner—Janice A. Howell
Assistant Examiner—David P. Porta
Attorney, Agent, or Firm—Douglas E. Stoner; James H. Beusse

[57] ABSTRACT

A scatter radiation compensation method for use in a medical diagnosis x-ray imaging system employs the use of an attenuating material placed in an x-ray beam to attenuate a portion of the beam such that the in-line component of the beam is reduced in the attenuated area. In one embodiment, an additional image is then taken utilizing an attenuator through out the full area of the beam to provide an image indicative of in-line components of the x-ray beam. The difference in image intensity between the two images is then computed to determine the scatter component of intensity and that intensity is thereafter substracted from the overall intensity obtained in a medical diagnostic image to obtain an image with the scattering effects removed. In one embodiment, the attenuating objects are plural spaced objects located at predetermined positions in the image. In a further embodiment, the image is taken through an attenuating object covering the entire beam, the object having a plurality of holes located at spaced intervals for permitting a portion of the beam to pass through unattenuated. In either embodiment, the component of scattering is determined by comparing the relative intensity values between the images developed with an object passing a portion of the beam unattenuated and an object passing an attenuated beam.

20 Claims, 5 Drawing Figures

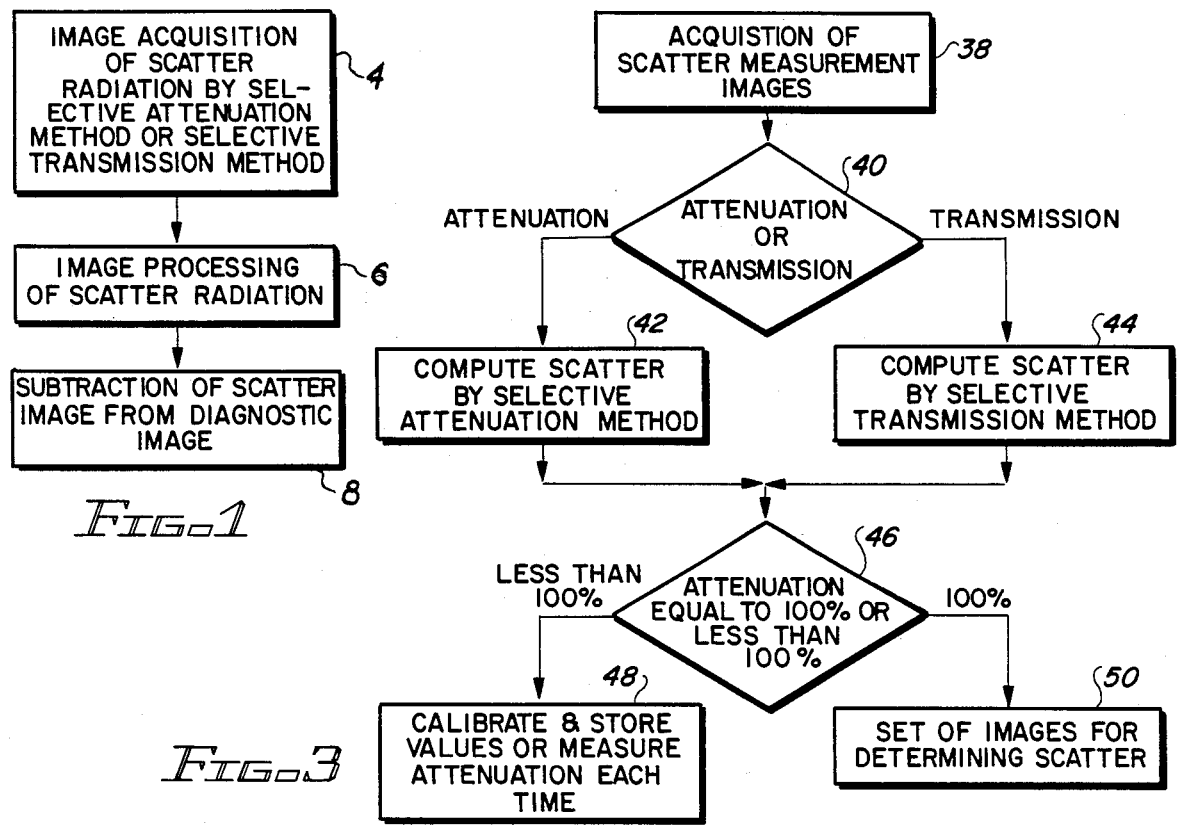
FIG-1
FIG-3
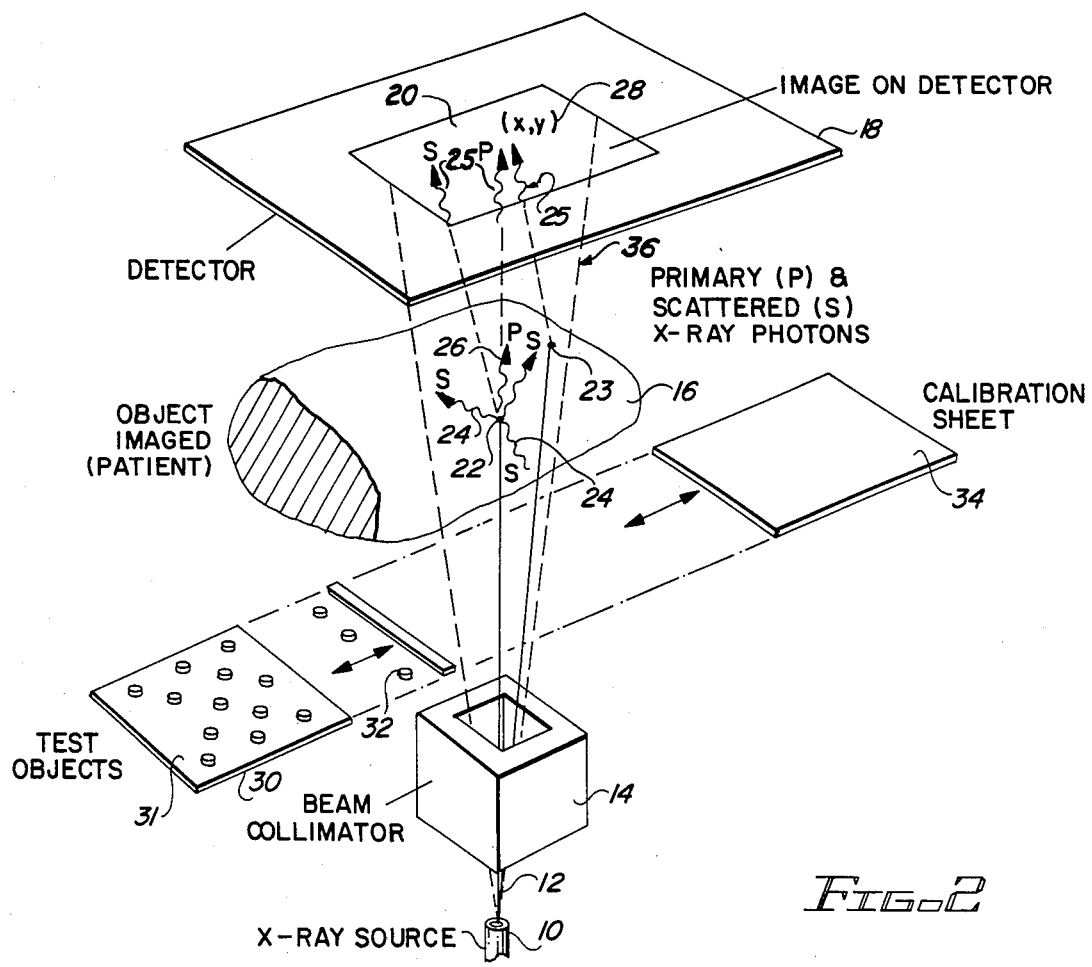
FIG-2

MEASUREMENT OF SCATTER IN X-RAY IMAGING

FIELD OF THE INVENTION

This invention generally relates to measuring the scattering of electromagnetic radiation and more particularly, to a method by which the scatter radiation effects in a medical diagnosis x-ray imaging system can be determined from the set of measurements made with the patient during the normal x-ray imaging procedure.

BACKGROUND DISCUSSION

A common characteristic of interactions between electromagnetic radiation and matter is the production of scatter radiation. Scatter radiation differs from incident radiation in at least one, and usually all of the following; direction of propogation, frequency (photon energy) and phase. In diagnostic imaging using x-ray radiation the scatter radiation has the deleterious effect of contributing to a measurement, e.g., film exposure, without contributing information. This comes about because the objective of diagnostic x-ray imaging is to measure the line integral of composite attenuation through a collection of points in the body along a path parallel to the x-ray beam. When this is done by exposing an area of the body at one time rather than making narrow beam point-by-point measurements, some of the scattered radiation produced reaches the measuring device. However, the point of interaction of the scattered ray with the measuring device bears no relation to the transmitted primary radiation which is being measured at that point. That is, the line integral of attenuation is being measured through primary beam transmission, making use of the fact that the transmitted primary radiation follows the trajectory of the incident beam. Scatter radiation trajectories, however, adhere to this trajectory only by chance. Thus, if the measuring device cannot discriminate between different angles of incidence for the incoming radiation, and cannot discriminate on the basis of photon energy or phase, the resulting measurement becomes corrupted by the contributions of scatter radiation.

Scatter radiation may differ from incident primary radiation in two other respects, photon energy and phase. The fact that scatter photon energies are always less than or equal to the primary photon energy is exploited in nuclear medicine imagery, where monochromatic sources are used and the detectors have an energy discrimination capability. In diagnostic x-ray imaging, however, the source is not monochromatic and energy discrimination is less practical. The typical x-ray tube emits a polychromatic spectrum, even at constant potential with significant filtration. The detectors, whether typical film/phosphor screen combinations, image intensifier tubes, solid-state detectors, or pressurized gases used in some detector arrays, exhibit rather broad spectral energy sensitivities. Even if the source were monochromatic, scatter rejection by pulse-height analysis would be limited with present technologies due to the photon flux rates which must be used in diagnostic imaging. Thus, although scatter radiation in x-ray imaging does exhibit a spectral shift toward lower energies compared to the incident primary radiation, it has not been practical to make use of this fact. The last opportunity for differentiation of scattering from primary radiation, i.e., phase, is precluded by both the lack of a phase-coherent source, e.g., a practical x-ray laser, and the lack of a practical phase-coherent detector. Thus, the primary means used to differentiate scattering from primary radiation has been beam trajectory.

In an area beam detector, which is an x-ray image receptor which can image a relatively large area of anatomy at one time, several schemes have been devised to selectively reduce scatter relative to primary radiation by using the fact that scattered beam trajectories diverge from the primary. Perhaps the simplest, and certainly the most common is the x-ray grid. A grid is simply an array of lead strips, separated by radiolucent material, which is focused on the focal spot of the x-ray tube. The grid is placed perpendicular to the x-ray beam between the patient and the detector. The focusing of the grid acts to preferentially accept primary radiation and reject scatter, due to the fact that the apparent origin of a scattering x-ray photon is not likely to be co-linear with the focal spot of the x-ray tube. While the grid improves the ratio of primary to scatter radiation, the increased x-ray tube power requirements and patient dose are a major disadvantage.

Other schemes to reduce scatter in area beam imaging have been attempted. In the slit-scan and scanning grid method, the x-ray beam is reduced to a slit by appropriate beam collimation, and then scanned across the area of interest. At the same time, and synchronous with the beam scanning, a slit window is scanned between the patient and detector. This method does offer improvements in scatter with minimal impact on patient dose, but x-ray tube requirements and imaging times are significantly increased.

In the techniques employed to reduce scatter, several important considerations arise. First, some compromise between scatter rejection and image acquisition time must be made. The tradeoff will depend on the rate of motion of the anatomy of interest. In early line-scan imaging of the brain, for example, scan times of five minutes were considered acceptable, while in coronary artery imaging, exposures longer than about 8 milliseconds may be unacceptable. Secondly, the finite output power capabilities of x-ray tubes pose practical limitations to narrow-beam and slit scan approaches, which require longer image acquisition times. The extent of scatter reduction which can be achieved in the image acquisition process, therefore, will be dictated by the exposure time constraints of the particular study.

Area detectors offer several significant advantages over line and point scanning systems despite the problems with scatter. These include: simultaneously imaging of large areas of anatomy, short exposure times, high image repetition rates, high utilization of limited x-ray tube power, and relative simplicity. The first four advantages are quite important clinically. The first two—simultaneous imaging of large areas and short exposure times—allow the diagnostician to image moving anatomy without motion blurring and without loss of timing or cause/event relationships. The third advantage—high image repetition rates—allows the assessment of dynamic changes in anatomy. The fourth advantage—power utilization—insures that the images obtained will have sufficiently high photon statistics to allow detection of significant contrast levels and details.

The advantages of the area beam imager lend it to multiple-energy imaging applications, where sets of images are acquired at different beam energies in order to form material-selective composite images. This is well described in the prior art. Scatter interferes with multiple-energy imaging in the ways already described, i.e., in reducing contrast and adding noise. In addition, scatter interferes with the formation of the material-selective image itself, producing the intensity variations which are dependent upon the scatter fraction at each point in the image. To correct the situation, the scatter component of intensity must be removed prior to the combination process. The potential applications of multiple-energy imaging include: angiography, intravenous pyelography, chest radiography, cholangiography and cholecystography, along with various other studies including detection of calcifications and abnormal tissue masses, such as tumor studies. Another potential application of material-selective imaging is bone marrow evaluation. In summary, scattering correction is essential to the process of material-selective image formation in area beam imagers, regardless of whether quantitative analysis of the resulting data is required.

The present invention is related to the prior art lead grid method of scatter correction in that it involves the use of x-ray absorbing test objects in the imaging field. Additional exposures using test objects are required. There are several practical considerations concerning the time in which the test and diagnostic images are acquired. First of all, the time required to gather the test object images must be less than the time in which significant patient motion can occur. Patient motion can be voluntary, respiratory, reflex or organ motion, such as motion of the heart or intestines. There are two approaches to handling organ motion, depending upon whether the motion is cyclic cardiovascular pulsation or random. In the case of cyclic motion of the vascular system, the x-ray exposures can be synchronized using an ECG, so that there is no observable motion between exposures. For the case of random motion, as in the intestines, techniques of motion reduction such as abdominal compression and intravenous administration of glucagon can be used. In all cases, minimizing the total time required for acquiring the test images will be advantageous.

Another consideration is the motion which may occur between the acquisition of the scatter measurement images and subsequent images to be corrected, such as contrast images in angiography. One would want the scatter distribution computed from the test object images to spatially register with the scatter distribution in subsequent images of interest. The scatter distribution is predominately a low-spatial frequency phenomena. That is, the intensity of scatter distribution does not vary significantly over short distances, as would the primary intensity in an area of anatomical detail. Thus, the scatter correction process should be relatively insensitive to small positional shifts in the scatter distribution, and therefore, patient motion. However, to minimize the possibility of such problems, the time between the acquisition of the test images and the actual study images is kept to a minimum. This implies that the scatter calculation and correction process is most effectively done after the total series of images has been acquired when time is not critical.

It is an object of the present invention to provide a method of scatter correction which can be applied after an image or images have been acquired. In this approach a set of test exposures is made to actually measure the level of scatter present at each point in the image. These test images may be acquired before or after the diagnostic image or images are acquired. The effect of the scatter is subsequently removed from diagnostic images by using the information gained from the test images.

It is a further object of this invention to enhance the x-ray imaging process by providing true primary attenuation data in imaging environments where scatter reduction in the acquisition process is limited due to exposure time constraints.

SUMMARY OF THE INVENTION

Two methods of scatter radiation measurements are described along with several variations within each method. In method one, an object of known contrast is introduced into the imaging field and its contrast in the presence of scatter is measured. The magnitude of the scatter can then be calculated by knowledge of both the true and apparent contrast of the test object. The method is unique in that the attenuation of the test objects used is less than 100%. This is important because it minimizes the disruption of the scatter distribution which one is trying to measure. Thus, to avoid altering the scatter distribution being measured, the size, shape, number and attenuation of the test objects are chosen carefully. The number of images of the test object which must be taken to measure the scatter distribution depends on the extent of the area which can be measured in a single exposure.

In method two, an object is introduced into the x-ray beam which attenuates the x-ray beam over the majority of the field incident to the patient. In this way, the scatter is reduced by the amount of the attenuation. However, one or more holes or openings exist within the object which allow the incident beam to reach the patient unattenuated. At these selected areas, the difference in measured intensity with or without the test object in the field allows the calculation of the scatter in that region. The attenuation of the test object may be 100% or less. The number of holes or openings and their size are chosen so as to minimize the effect on the scatter distribution.

When objects of less than 100% contrast are used in method one or method two, it is necessary to know the true contrast of the test object. The true contrast will depend on the conditions of the imaging situation, that is, the x-ray tube voltage, the x-ray source filtration, beam-hardening effects of the patient's anatomy, the grid and even the spectral sensitivity of the detector. There are two ways to address this problem. One is to calibrate the system over the range of x-ray tube voltage, filtration, patient size, etc. required for scatter measurement. The second way is to actually measure the test object contrast during the procedure by acquiring one image in the test sequence with a sheet of material of the same composition and thickness as the test objects used. This sheet of material will intercept the entire beam, thereby covering the entire image. In this way, both primary and scattered radiation will be attenuated and the true attenuation or contrast of the test material can be measured.

BRIEF DESCRIPTION OF THE DRAWINGS

FIG. 1 is a flow diagram which represents the main steps of the present invention.

FIG. 2 is a pictoral representation of the test objects placed in a radiation field between an x-ray source and a patient as an image is acquired.

FIG. 3 represents a detailed summary of the procedures for acquisition of images to measure scatter.

DETAILED DESCRIPTION OF AN ILLUSTRATIVE EMBODIMENT

A. General Description

Figure 4:
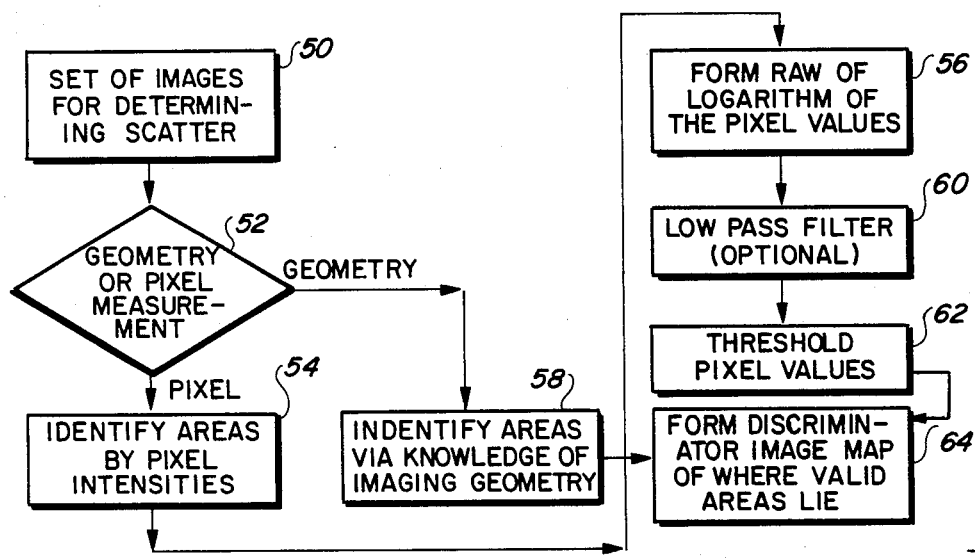
FIG. 4 represents a first portion of a detailed summary of the procedures for image processing of the images to measure scatter.

FIG. 1 represents a block diagram of the major steps in eliminating the scatter radiation from a medical diagnostic image. Block 4 represents the image of the scatter radiation being acquired by the selective attenuation method (described later). After the scatter radiation has been acquired, the image has to be processed to determine where the valid data lies in the scatter image acquired by the two acquisition methods, this is represented by block 6. Finally, after the scatter image has been processed, the scatter image is subtracted from the diagnostic image to remove the scatter radiation effect, to leave only an image due to primary radiation, as shown by block 8.

B. Formulation of Scatter Acquisition Methods

1. Formulation of the Line Integral of Attenuation

FIG. 2 is a pictoral representation of a medical x-ray image system. The details of the x-ray system are not important to understand the present invention. Thus, to avoid complexity, the exact details and operation of the x-ray image system are not included, but are well known in the art. An x-ray source 10 produces a polychromatic x-ray beam 12 that is limited by a beam collimator 14 to that portion directed toward an object 16. The x-ray beam 12 passes through the object 16 impinging on the detector 18. An area projection x-ray image 20 of object 16 is formed on the detector 18. The object 16 is commonly a patient or an area thereof in a medical x-ray imaging system. Scatter radiation 24 and 25 is shown being generated at points 22 and 23 within the object 16. The primary radiation 26 is shown incident upon the detector 18 along with the scatter radiation 24 and 25 in the image 20. The scatter radiation 25 reduces the contrast of the x-ray detail as can be seen on x-ray image 20, where the scatter radiation 25 from point 23 has combined with the primary radiation 26 to produce image 20 at point (x,y) 28. The problem is to measure the scatter radiation 25 and subtract its effect from the image 20.

The intensity of the image formed on the detector at any point (x,y) 28 and any time (t) is denoted by $I(x,y,t)$. $I(x,y,t)$ represents the integrated intensity response of the detector 18 to the polychromatic x-radiation incident to it. Therefore, there is no need to carry consideration of the polychromatic nature of the radiation beyond the formation of $I(x,y,t)$. The detected beam intensity, $I(x,y,t)$, contains contributions from both primary transmission and scattered radiation as follows:

$$I(x,y,t) = P(x,y,t) + S(x,y,t) \quad \text{(Eq. 1)}$$

where:
 $P(x,y,t)$ = Primary radiation component at (x,y)
 $S(x,y,t)$ = Scattered radiation component at (x,y)
 $(x,y)$ = A point (x,y) in the image
 $t$ = Time The primary transmitted radiation P indicated at 26 can be described by the incident beam intensity $Io(x,y,t)$ and the line integral of attenuation along the beam corresponding to the point (x,y) as follows:

$$P(x,y,t) = Io(x,y,t) EXP[-INT[up,dl]] \quad \text{(Eq. 2)}$$

where:
 $Io(x,y,t)$ = The incident beam intensity
 $EXP[\ ]$ denotes the exponential of the base e
 $INT[up,dl]$ denotes the integral of 'up' with respect to 'l'
 u = The mass attenuation coefficient of intervening material
 p = The density of intervening material
 l = Distance along the x-ray beam path through the intervening material In measuring an x-ray image, the parameter of interest is the line integral of attenuation $INT[up,dl]$. To compute $INT[up,dl]$, the incident intensity $Io(x,y,t)$ and the measured primary intensity $P(x,y,t)$ are needed. Given that the incident intensity can be measured, the line integral of attenuation can be obtained easily if the scatter is zero.

For $S(x,y,t) = 0$.

$$EXP[-INT[up,dl]] = P(x,y,t)/Io(x,y,t) \quad \text{(Eq. 3)}$$

$$INT[up,dl] = -LN[P(x,y,t)/Io(x,y,t)] \quad \text{(Eq. 4)}$$

where: $LN[\ ]$ denotes the natural logarithm. If the scatter component is not zero and is unknown, the determination of the line integral of attenuation is not possible, and in addition, the unknown scatter component cannot be carried along in the mathematics due to the natural log.

For $S(x,y,t)$ nonzero.

$$INT[up,dl] = -LN[[I(x,y,t) - S(x,y,t)]/Io(x,y,t)] \quad \text{(Eq. 5)}$$

Sometimes the total line integral of attenuation is not the parameter of interest but a specific change in this line integral due to the addition of some contrast material. This situation can be described as follows:

$$Pcon(x,y,t) = Io(x,y,t) EXP[-(INT[up,dl] + upl')] \quad \text{(Eq. 6)}$$

where:
 $Pcon(x,y,t)$ = Primary transmitted with added contrast
 $upl'$ = Linear attenuation of added contrast.
Adding the scatter component:

$$Icon(x,y,t) = Pcon(x,y,t) + Scon(x,y,t) \quad \text{(Eq. 7)}$$

where:
 $Icon(x,y,t)$ = Detected beam intensity with added contrast material $upl'$
 $Scon(x,y,t)$ = Detected scatter intensity with added contrast material $upl'$ In this situation, the images with and without the added contrast can be used to demonstrate the added contrast without showing the total attenuation profile of the object. This is done by dividing the two images or, equivalently, taking the logarithm of their intensity values and then subtracting them.

In the absence of scatter, the calculation is straightforward:

For S(x,y,t)=0
I(x,y,t)=P(x,y,t)

$$Icon(x,y,t) = Pcon(x,y,t) \quad (Eq.\ 8)$$

$$\frac{Icon(x,y,t)}{I(x,y,t)} = \frac{Io(x,y,t)EXP[-(INT[up,dl] + upl')]}{Io(x,y,t)EXP[-INT[up,dl]]}$$

$$= EXP[-upl']$$

$$upl' = LN[I(x,y,t)/Icon(x,y,t)]$$

Thus, in the absence of scatter, the calculation is relatively simple. With scatter present, the situation becomes more complex. In the following derivation, upl', the quantity of interest, will be expressed in terms of the measured intensity values and the scatter distributions.

Rearranging equations '1 and 7:

$$P(x,y,t)=I(x,y,t)-S(x,y,t)$$

$$Pcon(x,y,t)=Icon(x,y,t)-Scon(x,y,t)$$

Substituting equations 2 and 6:

$$Io(x,y,t)EXP[-INT[up,dl]]=I(x,y,t)-S(x,y,t) \quad (Eq.\ 9)$$

$$Io(x,y,t)EXP[-(INT[up,dl]+upl')]=Icon(x,y,t)-Scon(x,y,t) \quad (Eq.\ 10)$$

Dividing equation 9 by equation 10:

$$EXP[upl'] = \frac{I(x,y,t) - S(x,y,t)}{Icon(x,y,t) - Scon(x,y,t)} \quad (Eq.\ 11)$$

Thus, the scatter distributions, if nonzero, must be known in order to compute upl', the quantity of interest. For small values of contrast upl', or small areas of contrast, Scon(x,y,t) will be sufficiently close to S(x,y,t) to allow use of a single distribution which can be measured in the image without the added contrast.

2. Selective Attenuation Method for Scatter Measurements

Referring again to FIG. 2, test objects 32 and 34 are placed in the path of the x-ray beam 12 between the x-ray source 10 and the object (patient) 16 as an image 20 or a series of images is acquired. In the selective attenuation method, two objects are used. One consists of a set of attenuating objects 32 distributed through the x-ray beam field. This is called the scatter test object. The second is a uniform sheet 34 of material of the same composition and areal density (volume density times thickness) as the individual test objects. This is called the calibration sheet. With the object 16 (patient) present the test objects 32 are distributed in the field 36 of the x-ray beam 12. An image 20 (or series of images with the test objects placed in a sequence of positions in the area 36) is made and stored, then the test objects 32 are replaced by the calibration sheet 34. The contrast of the test objects is then determined by the image from the calibration sheet 34. The size, shape, number and attenuation of the test objects 32 are chosen to avoid altering the scatter distribution being measured.

In the normal imaging mode, that is, without any scatter measurement devices in the beam, I(x,y,t) can be expressed as follows:

$$I(x,y,t)=P(x,y,t)+S(x,y,t) \quad (Eq.\ 12)$$

where:
P(x,y,t)=Primary radiation component at (x,y,t)
S(x,y,t)=Scattered radiation component at (x,y,t)

First, the scatter test objects 32 are placed in the beam, (see FIG. 1), and the image intensity at (x,y,t) is measured. The equations describing the image intensity values in the region of each test object and outside the region of the object are derived by assuming that the scatter is essentially unaffected by the presence of the test object(s). The size, shape, number and attenuation of the test object(s) 32 are chosen by the following conditions:

(1) The percentage of the total imaged area blocked by the test objects is small.

(2) The contrast of the test objects is small.

(3) The area or areas blocked by the test objects are distributed through the total image area rather than concentrated in one location.

Under these conditions the equations which describe the image intensity values within the outside the projection of each test object are as follows:

Within test object:

$$Itest(x,y,t)=P(x,y,t)T(x,y,t)+S(x,y,t) \quad (Eq.\ 13)$$

where:
Itest(x,y,t)=Image intensity at (x,y,t) with test object intercepting beam
T(x,y,t)=Radiographic transmission of test object at (x,y,t).

Outside the test objects:

$$I(x,y,t)=P(x,y,t)+S(x,y,t)$$

which is simply equation 12.

Second, the calibration sheet 34 is placed in the beam in order to measure to true contrast of the test object and thereby calibrate the scatter correction process, the defining equation is given by:

$$Ical(x,y,t)=P(x,y,t)T(x,y,t)+S(x,y,t)T(x,y,t) \quad (Eq.\ 14)$$

where all the terms are as defined above.

The transmission of the calibration sheet 34 is allowed to vary in space and time. The variation in space is provided to allow for beam-hardening effects which could be introduced by the x-ray tube or any attenuation in the beam which is not uniform across the field. The variation allowed in time is provided to account for beam energy variations in time due to power variations, etc. In most cases, however, only the variation in space is necessary.

The next step is to derive the scatter distribution from the equations of the three types of images described above. First, the transmission of the test object material can be determined by dividing equation 14 by equation 12.

$$\frac{Ical(x,y,t)}{I(x,y,t)} = \frac{P(x,y,t)T(x,y,t) + S(x,y,t)T(x,y,t)}{P(x,y,t) + S(x,y,t)} \quad (Eq.\ 15)$$

$$= T(x,y,t)$$

With the transmission determined, an expression for scatter in terms of known quantities can be derived by subtracting equation 14 from equation 13.

$$I_{test}(x,y,t) - I_{cal}(x,y,t) = P(x,y,t)T(x,y,t) + S(x,y,t) - \quad \text{(Eq. 16)}$$

$$[P(x,y,t)T(x,y,t) + S(x,y,t)T(x,y,t)] = S(x,y,t)[1 - T(x,y,t)]$$

Combining equations 15 and 16:

$$S(x,y,t) = \frac{I_{test}(x,y,t) - I_{cal}(x,y,t)}{1 - I_{cal}(x,y,t)/I(x,y,t)} \quad \text{(Eq. 17)}$$

(Valid only in the region of a test object).

Thus, the scatter distribution can be calculated within the area projected by the test object by arithmetic manipulation of three images. In order to determine $S(x,y,t)$ for all $(x,y)$, it is necessary to either have a set of images [$I_{test}(x,y,t)$] which provide measurements of the test object transmission at every point in the image, or a set of images [$I_{test}(x,y,t)$] which sample the transmission of the test object at various points in the field, followed by interpolation. The size of this set of images could be one.

A special case of the Selective Attenuation Method (Method One) is to use 0% transmission material for the test object(s). In this case no calibration sheet or image thereof are required, and equation 17 reduces to:

ti $S(x,y,t) = I_{test}(x,y,t)$ \quad (Eq. 18)

Thus the scatter radiation is equal to the image intensity with the test object intercepting the beam. (Valid only in the region of a test object). This relation has already been described and utilized in the literature, and is presented here only to indicate that it is a special case of the general methods described here.

3. Selective Transmission Method for Scatter Distribution Measurement

In the selective transmission method for scatter distribution measurement, two test objects are used. The first object 30, always required, consists of an attenuating sheet 30 with a set of holes 31 or openings in it. This is the scatter test object for the hole method. The second is a uniform sheet of material 34 of the same composition and areal density (volume density times thickness) as the test object 30. This is called the calibration sheet 34, as in method one.

In the normal imaging mode, that is, without any scatter measurement devices in the beam, $I(x,y,t)$ can be expressed as follows:

$$I(x,y,t) = P(x,y,t) + S(x,y,t) \quad \text{(Eq. 19)}$$

where:
$P(x,y,t)$ = Primary radiation component at $(x,y,t)$
$S(x,y,t)$ = Scattered radiation component at $(x,y,t)$ First, the scatter test object 30 with holes is placed in the beam (see FIG. 2), the equations describing the image intensity values in the region of the holes and outside the region of the holes are derived by assuming that the scatter is essentially unaffected by the presence of holes in the test object, because the test object 30 is formulated by the following conditions:

(1) The percentage of the total imaged area occupied by the holes 31 in the test object sheet 30 is small.

(2) The contrast of the test object sheet 31 is small.

(3) The holes 31 in the test object are distributed through the total image area rather than concentrated in one location.

Under these conditions the equations which describe the image intensity values within the outside the projection of the holes in the test object are as follows:

Within a hole:

$$I_{htest}(x,y,t) = P(x,y,t) + S(x,y,t)T(x,y,t) \quad \text{(Eq. 20)}$$

where:
$I_{htest}(x,y,t)$ = Image intensity at $(x,y,t)$ with hole in test object intercepting beam
$T(x,y,t)$ = Radiographic transmission of test object in the area of the hole at $(x,y,t)$.

Outside holes in test object:

$$I(x,y,t) = P(x,y,t)T(x,y,t) + S(x,y,t)T(x,y,t) \quad \text{(Eq. 21)}$$

Second, the calibration sheet 34 is placed in the beam in order to measure the true contrast of the test object sheet 31 and thereby calibrate the scatter correction process. The defining equation is given by:

$$I_{cal}(x,y,t) = P(x,y,t)T(x,y,t) + S(x,y,t)(T(x,y,t)) \quad \text{(Eq. 22)}$$

where all the terms are as defined above.

The transmission of the hole test object and calibration sheet are allowed to vary in space and time. The variation in space is provided to allow for beam-hardening effects which could be introduced by the x-ray tube or any attenuation in the beam which is not uniform across the field. The variation allowed in time is provided to account for beam energy variations in time due to voltage variations, etc. In most cases, only the variation in space is necessary.

The next step is to derive the scatter distribution from the equations of the three types of images described above. First, the transmission of the test object material can be determined by dividing equation 22 by equation 19.

$$\frac{I_{cal}(x,y,t)}{I(x,y,t)} = \frac{P(x,y,t)T(x,y,t) + S(x,y,t)T(x,y,t)}{P(x,y,t) + S(x,y,t)} \quad \text{(Eq. 23)}$$

$$= T(x,y,t)$$

With the transmission determined, an expression for scatter in terms of known quantities can be derived by subtracting equation 20 from equation 19.

$$I(x,y,t) - I_{htest}(x,y,t) = P(x,y,t) + S(x,y,t) - [P(x,y,t) + \quad \text{(Eq. 24)}$$

$$S(x,y,t)T(x,y,t)] = S(x,y,t)[1 - T(x,y,t)]$$

Combining equations 15 and 20:

$$S(x,y,t) = \frac{I(x,y,t) - I_{htest}(x,y,t)}{1 - I_{cal}(x,y,t)/I(x,y,t)} \quad \text{(Eq. 25)}$$

(Valid only in the region of a hole).

Thus, the scatter distribution can be calculated within the area projected by the test object by arithmetic manipulation of three images. In order to determine $S(x,y,t)$ for all $(x,y)$, it is necessary to either have a set of images [$I_{htest}(x,y,t)$] which provide measurements of the intensity through a hole in the test object at every point in the image, or a set of images [$I_{htest}(x,y,t)$] which provide sample measurements at various points in the field, followed by interpolation.

A special case of Method 2 is to use a 0% transmission (100% attenuation) sheet for the test object with holes. In this case no calibration sheet or image thereof are required, and equation 25 reduces to:

$$S(x,y,t) = I(x,y,t) - Ihtest(x,y,t) \qquad \text{(Eq. 26)}$$

(Valid only in the region of a hole).

4. Summary of Image Acquisition Process

Referring to FIG. 3, the process and various alternatives for image acquisition are shown in block 38. Both Method 1, selective attenuation, and Method 2, selective transmission, are options, represented by block 40. If the attenuation method is chosen, block 42, the scatter image is computed by equations 12 through 18. If the transmission method is chosen, block 44, the scatter image is computed by equations 19 through (26). Whichever method is chosen, there is also the option to use complete (100%), or partial (less than 100%) attenuation for the test object(s), as shown by block 46. A further option is available in the case of using less than 100% attenuation. This is the option to either calibrate the image system such that the attenuation of the test object is known for all relevant x-ray techniques, or to introduce a calibration sheet of material into the beam around the time the test images are acquired, thereby measuring the attenuation under the actual imaging conditions, as repreented by block 48.

The end result of the image acquisition in each case is a set of images, or a single image, from which the scatter distribution can be determined as described in the following sections.

C. Image Processing Techniques

Referring to FIG. 4, the first problem to solve in processing the images produced from the acquisition methods is determining where the valid data lies in a test image. That is, the valid data in the test object areas must be extracted from the image or set of images used. represented by block 50. Two approaches are employed, as shown in block 52. The first is to use the knowledge of the imaging geometry to calculate where the test object(s) should lie in the image(s). This can be done by knowing the size and orientation of the object(s) in the test beam, the magnification of the imaging geometry, the sizing or minification of the image intensifier, optics, etc., as illustrated in block 58. The second approach, block 54, is to find the object(s) in the image through image processing. The latter approach is detailed in the following section.

1. Formation of the 'Discriminator' Image

In this section, a method is described whereby an image indicating where the valid test object sample areas are located is formed. The image so formed will be called a 'Discriminator' image having the property that its pixel values take on one value (nominally 1) in valid test object sample areas, and another value (nominally 0) outside these areas.

As shown in block 56, there are two approaches— one which uses the raw pixel values and another which takes the logarithm of the pixel values to equalize the signal produced by the test object over the range of intensity values encountered. In addition, the images combined to arrive at the discriminator image depend upon whether the selective attenuation or selective transmission method is used.

FOR SELECTIVE ATTENUATION:

The image $I(x,y,t) - Itest(x,y,t)$ or, alternately $LN[I(x,y,t)] - LN[Itest(x,y,t)]$ is formed.

FOR SELECTIVE TRANSMISSION, ATTENUATION <100%:

The image $Ihtest(x,y,t) - Ical(x,y,t)$ or, alternately $LN[Ihtest(x,y,t)] - LN[Ical(x,y,t)]$ is formed.

FOR SELECTIVE TRANSMISSION, ATTENUATION = 100%.

The image $Ihtest(x,y,t)$ or, alternately, $LN[Ihtest(x,y,t)]$ is formed.

The net result of these manipulations is to generate an image whose intensity values indicate the presence or absence of the test object or hole. Subtraction is used to eliminate variations in intensity due to the scene (patient) being imaged. The resulting image, then, is an image of the test object itself. Following this process, the image may be low-pass filtered spatially to reduce image noise, as shown in block 60. This can improve the next step, which is thresholding.

The image formed as described above is subjected to a thresholding operation, block 62, whereby pixel values lower than the threshold value are set to one value (nominally 0), and pixel values equal to or greater than the threshold value are set to another value (nominally 1). This is the 'Discriminator' image, block 64, described previously which will be used to extract the useful scatter sample data. As can be seen in FIG. 4, the alternate process of using the imaging geometry to calculate where the test object sample areas lie produces a 'Discriminator' image. The following section describes an optional step for improving the quality of the 'Discriminator' image.

2. The Edge Clip Function

Due to the imperfections inherent in the x-ray imaging system, the edges of the test object or the holes in it are blurred. The pixel values in the region of the blurring are not valid, since they do not fit the assumptions previously presented of the scatter measurement derivation.

Figure 5:
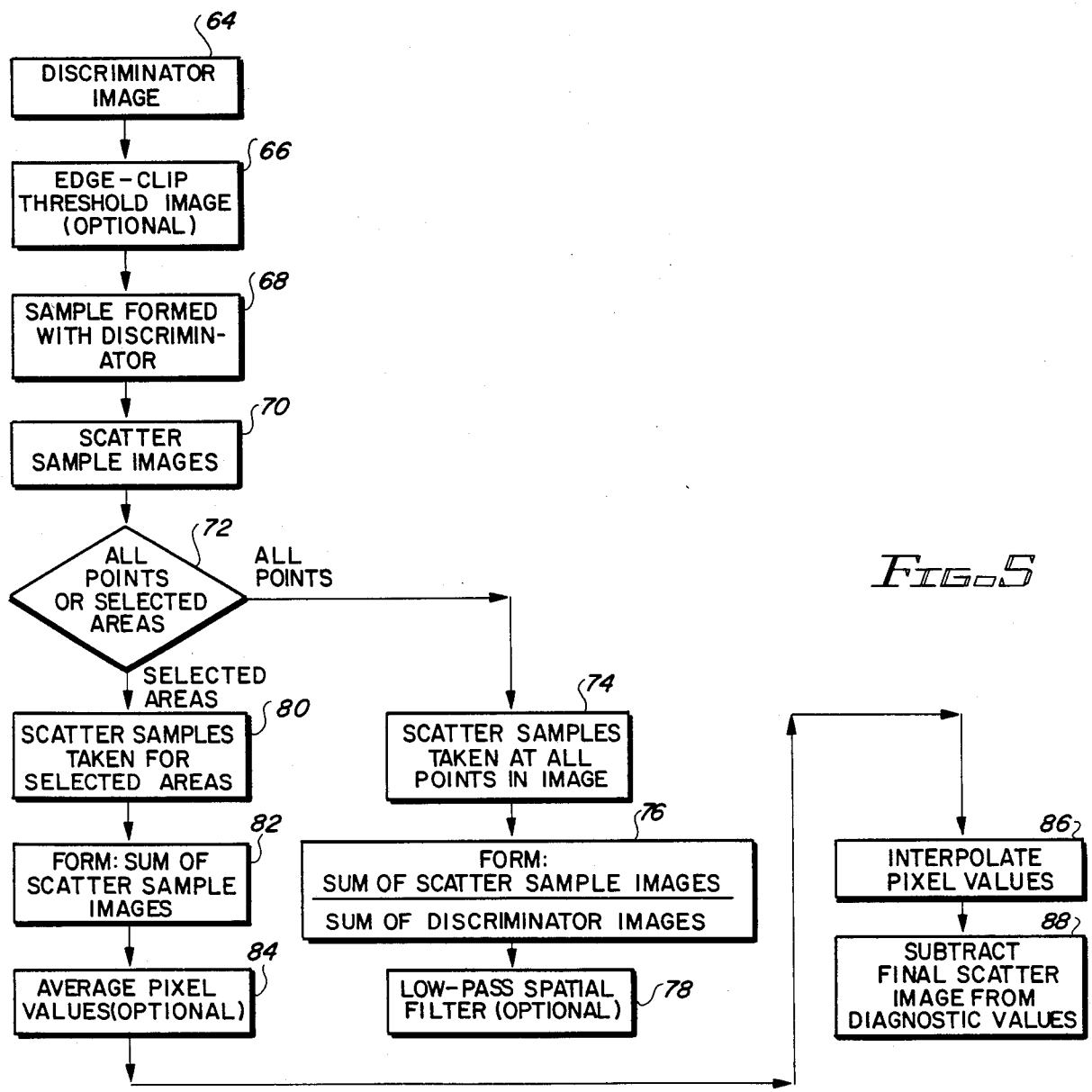
FIG. 5 illustrates a second portion of the procedure for image processing of the scatter images.

Referring to FIG. 5, a process described as a 'logical convolution' is used to eliminate the edge values, shown in block 66. First, the discriminator image is shifted some number of pixels in the 'x' and/or 'y' direction. Then each shifted Discriminator image pixel value is logically 'ANDed' with the corresponding pixel value in the unshifted discriminator image. Only those pixels whose values indicate the presence of a sample area in both the unshifted and shifted discriminator will continue to indicate the presence of the sample area. This process is repeated for a collection of shifts in some neighborhood of the central point, e.g., a 3×3 matrix. In this way, pixels which lie at the edge of a sample area will be set to a value (nominally 0), thereby dropping them from the sample area. This process essentially shrinks the test object sample areas identified in the discriminator image, thereby eliminating the points at the edges of the sample areas which are corrupted by blurring.

As a specific example for illustrative purposes, assume that a Discriminator image $D(x,y)$ exists whose pixel values are "1" in detected scatter sample areas and "0" elsewhere. For this case, a 3×3 edge-clipped Discriminator image $Dc(x,y)$ is formed as follows:

$Dc(x,y) = D(x,y)$ AND $D(x+1,y)$
AND $D(x,y+1)$ AND $D(x+1,y+1)$
AND $D(x-1,y)$ AND $D(x-1,y-1)$ AND $D(x-1,y-1)$

AND D(x,y−1) AND D(x+1,y−1)
where 'AND' is the logical 'AND' function

The only pixels in Dc(x,y) which have a value of one are those whose corresponding pixels in D(x,y) have the property that their value and the value of all their adjacent neighbors is one.

3. Formation of the Image to be Sampled by the Discriminator

It is necessary to form an image whose pixel values in the scatter sample areas represent the amount of scatter present, as shown in block 70. The method of formation depends upon whether the selective attenuation method (Method 1) or the selective transmission method (Method 2) is used. The details of the process were given in the sections "Selective Attenuation Method" and "Selective Transmission Method". The appropriate equations are equation 17 for selective attenuation, equation 25 for selective transmission with attenuation 100% and equation 26 for selective transmission with attenuation=100%.

The valid scatter information is extracted from the image formed in the previous section using the Discriminator image as follows. Each pixel in the scatter sample image is compared to the corresponding pixel (same x,y value) in the Discriminator image. If the value of the pixel in the Discriminiator image is zero, the pixel value in the scatter sample image is set to zero. If the value of the pixel in the Discriminator is one, the pixel value in the scatter sample image is left unchanged. The net effect is that the value of all pixels outside the recognized valid scatter sample areas is set to zero. The only nonzero pixel values represent valid scatter. This process is shown as block 68.

D. Integrating Multiple Measurements

It was stated that several test object images may be required to adequately determine the scatter distribution. When this is the case, the scatter information extracted from this set of images must be combined to form a composite scatter image. A further complication occurs when there are multiple measurements of scatter at any given point, that is, when the scatter measurements overlap. These two cases will be considered separately, as shown by block 72.

1. Overlapping Scatter Sample Areas

If one chooses to measure the scatter at all points in the image, block 72, rather than to sample and interpolate the results, the scatter sample areas must overlap for practical reasons. This poses the problem of having multiple measurements of scatter in the overlapping regions between scatter sample regions. This can be handled by keeping track of the number of scatter measurements taken for each pixel by, e.g., simply adding the set of Discriminator images together. If a pixel has only one sample, its value in the summed discriminator image will be one. If a pixel was sampled twice, its value will be two, etc.

The composite scatter sample image is formed by dividing the sum of the individual scatter sample images by the sum of the individual Discriminator images, as shown in block 76. This can be represented as follows:

$$Sc(x,y) = \frac{\text{Sum of } Si(x,y)}{\text{Sum of } Di(x,y)}$$

where:
  Sc(x,y)=Composite scatter sample image
  Si(x,y)=The i'th individual scatter sample image
  Di(x,y)=The i'th individual Discriminator image In the case where the composite scatter sample image Sc(x,y) contains measurements from each point in the image, the image could be spatially low-pass filtered to reduce the photon statistical noise, as shown in block 78. This would be practical because the scatter distribution should not contain high spatial frequency components which would be adversely affected by filtering.

2. Non-overlapping Scatter Sample Areas

If the sample areas do not overlap, the composite scatter image can be formed by simply adding the sampled scatter images together. Since the pixel values have been set to zero outside the valid sample areas, each image will contribute only valid sample data to the composite image.

In this case, the composite scatter sample image does not contain scatter measurements for each point in the image, block 80, interpolation between the valid sample values is the preferred method. The details of the interpolation process, along with some additional processing options is given in the following two sections. These two sections apply only to the case where the valid scatter samples do not cover the entire image, that is, where the intent is to interpolate between the samples rather than make x-ray measurements over the entire image.

3. Averaging of Scatter Sample Areas

A first step prior to the interpolation process is shown in block 82. Although not essential to the interpolation process, it is useful in reducing the number of computations required in the interpolation process itself. It therefore affords some economies in processing time and memory requirements.

In this step, the scatter sample image is broken up into a coarse grid, or collection of areas. These may be square, rectangular, etc. Then, a process is initiated whereby the nonzero pixels within each region are averaged together and counted. In addition, the geometric centroid of the nonzero pixels in the region is computed (as per the understood definition of the centroid). Then, the set of nonzero pixels in each region is replaced by the average of those pixels with the coordinates of the centroid of the original nonzero pixels' distribution, as shown in block 84. In this way the number of points to be entered into the interpolation is substantially reduced. Once again, the assumption that the scatter distribution is slowly-varying in space is used to make this simplification possible.

4. Interpolation of Scatter Samples

Interpolation of the scatter samples may be accomplished by any of the traditional, well-known methods, as shown in block 86. Perhaps the best is the minimum mean-squared error fit to an analytic function, such as an nth order two dimensional polynomial. A further refinement which may be used when the pixel values have been averaged together as described in the preceeding section, is to weigh the averaged pixel values in the mean-square error calculation with the number of pixels contributing to that average. This allows the larger scatter sample areas (with better statistics) to have more influence on the interpolated fit than the smaller areas.

E. Substration of Scatter Distribution From Diagnostic Images

Once the scatter distribution has been determined through one of the methods described herein, it is subtracted from the diagnostic image(s) taken immediately before or after the scatter measurement test exposures, as shown in block 88. The diagnostic images with scatter subtracted will have pixel intensity values which are truly representative of the attenuation encountered by the primary beam at that point.

The image system point-spread function or alternately, the modulation transfer function in the frequency domain, must be considered whenever intensity measurements are made on an image. The system point-spread (PSF) has the effect of modifying the true value of intensity at any point in an image by adding in a weighted sum of the intensity values of neighboring points or pixels. This has the effect of preferentially distorting the data in regions where considerable high frequency components are present, such as edges or sharp boundaries. The system PSF is the convolution of the PSF's of the individual contributing elements, which include: the x-ray tube focal spot, motion of patient relative to x-ray tube or detector, and a composite PSF of the detector, which includes the image intensifier, optics, video camera, anti-aliasing filter and a/d converter. Initial investigations have shown that the unwanted effect of system PSF can be virtually eliminated by appropriate choice of test object dimensions. In short, the effect of system point-spread function is negligible if the size of the test object samples or holes are large compared to the spread of the point-spread function. This insures that the majority of points used for measurement are unaffected by the PSF. The PSF affects the measurements at the edge of the test object samples or holes which can be excluded from the calculation.

Although the invention has been described in what is presently considered a preferred embodiment, it will be apparent that modification and variation may be made without departing from the spirit and scope thereof. It is intended therefore that the invention be interpreted in light of the appended claims.

What is claimed is:

1. In a medical diagnosis x-ray imaging system with scatter radiation effects, the system having an x-ray source transmitting a collimated beam through a first object for producing a first intensity image onto an image detector, a method for calibrating the first intensity image by measuring a scatter radiation intensity image comprising the steps of:
   (A) positioning a plurality of second objects in the collimated beam to attenuate a corresponding plurality of dispersed areas of the beam to produce a second intensity image on the image detector, the attenuation of each of the second objects being less than 100 percent in the x-ray frequency spectrum;
   (B) replacing the plurality of second objects with a uniform sheet of material of identical composition and areal density as the second objects to produce a third image intensity onto the image detector;
   (C) generating the scatter radiation intensity image from the first, second and third intensity images; and
   (D) subtracting the scatter radiation intensity image from the first intensity image to remove any scattering effects in order to calibrate the first intensity image.

2. The method in claim 1, wherein the first intensity image comprises a medical diagnostic image, the first object corresponding to a patient.

3. The method in claim 1, wherein the step (C) of generating further comprises the steps of:
   (A) providing data identifying at least the geometry, magnification, and minification characteristics of the x-ray imaging system;
   (B) providing data identifying the plurality of second objects, the data including the dimensions and orientation of the plurality of second objects; and
   (C) computing a position of each of the plurality of second objects in the second intensity image from the x-ray system and the dimensions of the plurality of second objects.

4. A method as in claim 1, having the image comprised of an array of pixels, wherein the step (C) of generating further comprises the steps of:
   (A) generating a discriminator image from any variation in intensity between the first intensity image and the second intensity image so that the discriminator image produces intensity values indicative of presence or absence of the plurality of second objects.

5. A method as in claim 4, further comprising the steps of:
   (A) filtering the discriminator image through a low-pass spatial filter to reduce image noise;
   (B) determining a pixel value for each pixel in the discriminator image pixel array, pixel values lower than a predetermined value being set to one value, and pixel values greater than a predetermined value being set to another value.

6. A method as in claim 5 wherein the one and another values are binary values, further comprising the steps of:
   (A) storing the discriminator image pixel array;
   (B) shifting the discriminator pixel image array a predetermined number of pixels in one direction of the array;
   (C) shifting the discriminator image pixel array a predetermined number of pixels in the other direction of the array;
   (D) logically ANDing each shifted discriminator image pixel value with the corresponding pixel value in the stored discriminator image pixel array in order to eliminate any pixel values corrupted by blurring of the edges of the plurality of second objects.

7. A method as in claim 6, further comprising the steps of:
   (A) generating from the first intensity image and the discriminator image the scatter radiation intensity image having each pixel value of the scatter radiation intensity image set to zero when the corresponding pixel value of the first intensity image is zero and the corresponding pixel value in the discriminator image is zero, and having each pixel value of the scatter radiation intensity image set to the corresponding pixel value of the first intensity image when the corresponding pixel value in the discriminator image is one.

8. In a medical diagnosis x-ray imaging system with scatter radiation effects having an x-ray source transmitting a collimated beam through a first object for producing a first intensity image onto an image detector, a method for calibrating the first intensity image by measuring a scatter radiation intensity image comprising the steps of:

(A) positioning a second object, having a plurality of dispersed openings to allow passage of a corresponding plurality of unattenuated beam areas, in the beam to attenuate a large area of the beam to produce a second intensity image such that the unattenuated beam areas are not concentrated in one location on the image detector, the attenuation of the second object outside the area of each opening being less than 100 percent in the x-ray frequency spectrum;

(B) replacing the second object with a uniform sheet of material of identical composition and areal density as the second objects to produce a third image intensity onto the image detector;

(C) generating the scatter radiation intensity image from the first, second and third intensity images;

(D) subtracting the scatter radiation intensity image from the first intensity image to remove any scattering effects in order to calibrate the first intensity image.

9. A method in claim 8, wherein the steps (C) of generating further comprises the steps of:

(A) providing data identifying at least geometry, magnification, and minification characteristics of the x-ray imaging system;

(B) providing data identifying the second object, the data including dimension and orientation of the second object; and (C) computing a position of the second object in the second intensity image from the x-ray system and the dimension of the second object.

10. A method as in claim 9, having the image comprised of an array of pixels, wherein the step (C) of generating further comprises the steps of:

(A) generating a discriminator image from any variation in intensity between the second intensity image and the third intensity image so that the discriminator image produces intensity values indicative of presence or absence of the second object.

11. A method as in claim 10, further comprising the steps of:

(A) filtering the discriminator image through a low-pass spatial filter to reduce image noise;

(B) determining a pixel value for each pixel in the discriminator image pixel array, pixel values lower than a predetermined value being set to one value, and pixel values greater than a predetermined value being set to another value.

12. A method as in claim 11 wherein the one and another values are binary values, further comprising the steps of:

(A) storing the discriminator image pixel array;

(B) shifting the discriminator pixel image array a predetermined number of pixels in one direction of the array;

(C) shifting the discriminator image pixel array a predetermined number of pixels in the other direction of the array;

(D) logically ANDing each shifted discriminator image pixel value with the corresponding pixel value in the stored discriminator image pixel array, in order to eliminate any pixel values corrupted by blurring of the edges of the second object.

13. A method as in claim 12, further comprising the steps of:

(A) generating from the first intensity image and the discriminator image the scatter radiation intensity image having each the pixel value of the scatter radiation intensity image set to zero when the corresponding pixel value of the first intensity image is zero and the corresponding pixel value in the discriminator image is zero, and having each pixel value of the scatter radiation intensity image set to the corresponding pixel value of the first intensity image when the corresponding pixel value in the discriminator image is one.

14. In a medical diagnosis x-ray imaging system with scatter radiation effects having an x-ray source transmitting a collimated beam through a first object for producing a first intensity image onto an image detector comprised of an array of pixels, a method for calibrating the first intensity image by measuring a scatter radiation intensity image comprising the steps of:

(A) positioning a second object in the beam to attenuate a small area of the beam to produce a second intensity image having a reduced intensity in the area corresponding to a position of the second object, the attenuation of the second object being less than 100 percent in the x-ray frequency spectrum;

(B) replacing the second object with a uniform sheet of material attenuating the entire beam, the sheet of material having identical composition and areal density as the second object, to produce a third image intensity onto the image detector;

(C) generating a discriminator image from any variation in intensity between the first intensity image and the second intensity image so that the discriminator image produces intensity values indicative of presence or absence of the second object;

(D) repeating step (A) through step (C) to generate a plurality of discriminator images corresponding to a plurality of second intensity images;

(E) forming a sum of the plurality of second intensity image;

(E) forming a sum of the plurality of the discriminator images;

(G) dividing the sum of the plurality of second intensity images by the sum of the plurality of the discriminatory images to produce a composite scatter intensity image; and (H) subtracting the composite scatter radiation intensity image from the first intensity image to remove any scattering effects in order to calibrate the first intensity image.

15. A method as in claim 14, wherein the step (G) further comprises the steps of:

(A) generating a plurality of geometric areas of nonzero pixel values of the composite scatter intensity image;

(B) determining a geometric centroid of each of the geometric areas;

(C) replacing the nonzero pixel values within each of the geometric areas by a single pixel at the geometric centroid of each of the areas having a value equal to an average value of the pixels in a respective one of the areas; and (D) generating a new composite scatter intensity image from a minimum mean squared error fit to an analytic function in two dimensions of the pixel array.

16. In a medical x-ray diagnosis system with scatter radiation effects, the system having an x-ray source transmitting a collimated beam for producing an image on an image detector, a method for correcting the image for scatter effects comprising the steps of:

(A) generating a diagnostic image of a patient having a first intensity on the image detector by interposing the patient in the x-ray beam impinging on the detector;

(B) generating a first test image by inserting an attenuator having less than one hundred percent attenuation at x-ray frequencies into the beam passing through the patient, the attenuator attenuating predetermined dispersed areas of the beam corresponding to locations of the attenuators to form a reduced intensity image in said locations;

(C) measuring the image intensity in said locations;

(D) determining the difference in measured intensity of the image in said locations and an intensity proportional to a predetermined attenuation of the attenuator; and subtracting the determined difference from the diagnostic image to correct for x-ray scatter.

17. In a medical x-ray diagnosis system with scatter radiation effects, the system having an x-ray source transmitting a collimated beam for producing an image on an image detector, a method for correcting the image for scatter effects comprising the steps of:

(A) generating a diagnostic image of a patient having a first intensity on the image detector by positioning the patient in the x-ray beam impinging on the detector;

(B) generating a first test image by inserting a first attenuator into the beam passing through the patient at predetermined dispersed positions;

(C) determining an intensity of the first test image in areas of the detector corresponding to the positions of the first attenuator;

(D) generating a second test image by inserting a second attenuator having identical attenuation characteristics as the first attenuator into the beam so as to attenuate the entire beam;

(E) determining the intensity of the second test image in the areas of the detector corresponding to the positions of the first attenuator;

(F) subtracting the intensity obtained in step (E) of determining from the intensity obtained in step (C) of determining to yield an intensity corresponding to the effects of scatter radiation; and (G) subtracting the scatter radiation intensity from the intensity of the diagnostic image to yield a scatter corrected image.

18. The method of claim 17 wherein the first attenuator comprises a plurality of dispersed objects having an attenuation less than 100 percent in the x-ray spectrum.

19. The method of claim 18 wherein the first attenuator comprises a sheet of attenuating material having a plurality of dispersed openings, the material having an attenuation less than 100 percent in the x-ray spectrum.

20. The method of claim 17 wherein the step (F) includes the steps of:

(A) generating a plurality of geometric areas of nonzero pixel values of the composite scatter intensity image;

(B) determining a geometric centroid of each of the geometric areas;

(C) replacing the nonzero pixel values within each geometric area by a single pixel at the geometric centroid of each of the areas having a value equal to an average value of the pixels in a respective one of the areas; and (D) generating a new composite scatter intensity image from a minimum mean squared error fit to an analytic function in two dimensions of the pixel array.

* * * * *